(12) United States Patent
Brennan et al.

(10) Patent No.: US 8,047,839 B2
(45) Date of Patent: Nov. 1, 2011

(54) METHODS OF IDENTIFYING ORTHODONTIC ADHESIVES

(75) Inventors: Joan V. Brennan, Sierra Madre, CA (US); Philip P. Soo, Fullerton, CA (US); Rajdeep S. Kalgutkar, Woodbury, MN (US); Rehan A. Suhrwardy, Fullerton, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 824 days.

(21) Appl. No.: 11/318,174

(22) Filed: Dec. 23, 2005

(65) Prior Publication Data

US 2007/0148609 A1 Jun. 28, 2007

(51) Int. Cl.
*A61C 3/00* (2006.01)
(52) U.S. Cl. ............................. 433/2; 433/215
(58) Field of Classification Search .......... 433/24, 433/9, 215, 228.1, 226, 217.1; 523/118, 523/120, 213, 204, 208; 106/35; 156/701, 156/281; 424/10.1

See application file for complete search history.

(56) References Cited

U.S. PATENT DOCUMENTS

| | | | |
|---|---|---|---|
| 3,729,313 A | 4/1973 | Smith | |
| 3,741,769 A | 6/1973 | Smith | |
| 3,808,006 A | 4/1974 | Smith | |
| 4,250,053 A | 2/1981 | Smith | |
| 4,394,403 A | 7/1983 | Smith | |
| 4,952,204 A | 8/1990 | Korteweg | |
| 5,269,682 A * | 12/1993 | Kesling | ............................ 433/24 |
| 5,545,676 A | 8/1996 | Palazzotto et al. | |
| 6,105,761 A | 8/2000 | Peuker et al. | |
| 6,413,087 B1 | 7/2002 | Petrich et al. | |
| 6,444,725 B1 | 9/2002 | Trom et al. | |
| 6,528,555 B1 * | 3/2003 | Nikutowski et al. | ........... 523/116 |
| 6,670,436 B2 | 12/2003 | Burgath et al. | |
| 6,960,079 B2 | 11/2005 | Brennan et al. | |
| 2002/0106334 A1 | 8/2002 | Combe et al. | |
| 2005/0203207 A1 | 9/2005 | Klettke et al. | |
| 2005/0214720 A1 | 9/2005 | Milanovich et al. | |
| 2006/0194172 A1 * | 8/2006 | Loveridge | ...................... 433/215 |
| 2008/0299519 A1 * | 12/2008 | Craig et al. | ................. 433/217.1 |

FOREIGN PATENT DOCUMENTS

| | | |
|---|---|---|
| WO | WO 2004/069944 | 8/2004 |
| WO | WO 2004/072194 A1 | 8/2004 |

OTHER PUBLICATIONS

"McCormick—Product Detail—Assorted Food Colors & Egg Dye" datasheet [online]. McCormick & Co., Inc., Sparks, Maryland, copyright 2003 [retrieved on Dec. 18, 2005]. Retrieved from the Internet:<URL:http://cftest.mccormick.com/mc2stage/productdetail.cfm?id-6034>; 1 pg.

(Continued)

*Primary Examiner* — Cris L Rodriguez
*Assistant Examiner* — Sunil K Singh
(74) *Attorney, Agent, or Firm* — Philip P. Soo (57) ABSTRACT

The present invention provides a method of identifying an orthodontic adhesive on a tooth structure, the method including selectively staining a surface including the orthodontic adhesive or the tooth structure. Methods of bonding and debonding an orthodontic appliance to and from a tooth structure are also provided.

12 Claims, 1 Drawing Sheet
(1 of 1 Drawing Sheet(s) Filed in Color)

OTHER PUBLICATIONS

"McCormick—Product Detail—Green Food Color" datasheet [online]. McCormick & Co., Inc., Sparks, Maryland, copyright 2003 [retrieved on Dec. 18, 2005]. Retrieved from the Internet: <URL:http://cftest.mccormick.com/mc2stage/productdetail.cfm?id=6036>; 2 pgs.

"McCormick—Product Detail—Yellow Food Color" datasheet [online]. McCormick & Co., Inc., Sparks, Maryland, copyright 2003 [retrieved on Dec. 18, 2005]. Retrieved from the Internet: <URL:http://cftest.mccormick.com/mc2stage/productdetail.cfm?id=6038>; 1 pg.

"McCormick—Product Detail—Red Food Color" datasheet [online]. McCormick & Co., Inc., Sparks, Maryland, copyright 2003 [retrieved on Dec. 12, 2005]. Retrieved from the Internet: <URL:http://cftest.mccormick.com/mc2stage/productdetail.cfm?id=6037>; 1 pg.

"McCormick—Product Detail—Blue Food Color" datasheet [online]. McCormick & Co., Inc., Sparks, Maryland, copyright 2003 [retrieved on Dec. 18, 2005]. Retrieved from the Internet: <URL:http://cftest.mccormick.com/mc2stage/productdetail.cfm?id=6035>; 1 pg.

* cited by examiner

METHODS OF IDENTIFYING ORTHODONTIC ADHESIVES

BACKGROUND

Orthodontic treatment involves movement of malpositioned teeth to orthodontically correct positions. Tiny orthodontic appliances, known as brackets, are connected to anterior, cuspid and bicuspid teeth, and an archwire forms a track to guide movement of the teeth to desired positions. In previous years, the orthodontic appliances were connected to teeth by welding or brazing each orthodontic appliance to a metal band, which was then placed on the desired tooth. But, more recently, it has been preferred to bond the brackets directly to the tooth surface. The direct bonding method minimized the use of metal band thus eliminating the "metallic mouth" appearance that is often associated with orthodontic treatment.

The use of a bonding method may typically require, among other steps, placing an amount of orthodontic adhesive on the bracket, applying the brackets to the desired, preferably preconditioned teeth, and removing excess orthodontic adhesive. Conventional orthodontic adhesives are typically clear or contain pigment, which gives the orthodontic adhesives a white or tooth color. It is desirable that a sufficient but not an excess amount of orthodontic adhesive is used to bond the brackets to the teeth surface. Excess orthodontic adhesive on the teeth may eventually be a site for bacteria accumulation. Because orthodontic treatment may last from 18 to 36 months or more, the bacteria accumulation may damage the teeth and may lead to discoloration of the orthodontic adhesive, both of which may be undesirable. Removal of the excess orthodontic adhesive from teeth surfaces may be difficult if there is similarity in the orthodontic adhesive color and the teeth color due to a lack of a contrasting color in the orthodontic adhesive.

Orthodontic adhesives with high bond strengths may lead to other difficulties. For example, one of the most difficult aspects of the orthodontic treatment process may be the removal of the bracket after completion of treatment. It is well known in the industry that certain adhesives, used in combination with certain rigid brackets, are capable of causing enamel fracture under some debonding conditions. As a result, many commercially available ceramic brackets have been designed for the bond to fail at the interface between the bracket and the adhesive to prevent damage to the tooth surface during the debonding process. This approach results in most of the cured adhesive pad being left behind on the tooth surface after the bracket has been removed. Removal of the adhesive pad, which is typically hard and heavily crosslinked, may be time consuming for the clinician and uncomfortable for the patient.

As with the unhardened orthodontic adhesive, the removal of the cured orthodontic adhesive from teeth surfaces may be difficult if there is similarity in the cured orthodontic adhesive color and the teeth color due to a lack of a contrasting color in the orthodontic adhesive.

A need remains for a method that effectively distinguishes unhardened and/or hardened orthodontic adhesive from the tooth surface to enable easy removal of the orthodontic adhesive by the practitioner.

SUMMARY OF THE INVENTION

In one aspect, the present invention provides a method of identifying an orthodontic adhesive on a tooth structure. In one embodiment, the method includes selectively staining a surface including the orthodontic adhesive or the tooth structure. Preferably the method includes selectively staining to provide a stained surface and an unstained or lightly stained surface (as used herein, a "lightly stained" surface means a surface that is lighter in color than an adjacent stained surface). The stained and/or unstained or lightly stained surfaces can be useful for visually identifying excess orthodontic adhesive and to aid in the removal thereof by methods known in the art.

In some embodiments, an orthodontic disclosing composition including a colorant can be used for selectively staining a surface including the orthodontic adhesive (e.g., unhardened or hardened) or the tooth structure. The orthodontic disclosing composition (e.g., a solution, a dispersion, or a suspension) can be applied to at least a portion of the orthodontic adhesive and/or at least a portion of the tooth structure by a variety of application methods known in the art.

In another aspect, the present invention provides a method of bonding an orthodontic appliance to a tooth structure. The method includes: providing an orthodontic appliance having a base for bonding the orthodontic appliance to a tooth structure and an orthodontic adhesive on the base thereof; applying the base of the orthodontic appliance to the tooth structure; and selectively staining a surface including the orthodontic adhesive or the tooth structure. Preferably the method includes selectively staining to provide a stained surface and an unstained or lightly stained surface. The stained and/or unstained or lightly stained surfaces can be useful for visually identifying excess orthodontic adhesive, which can then be removed. In some embodiments, an orthodontic disclosing composition including a colorant can be used for selectively staining the surface including the orthodontic adhesive (e.g., unhardened or hardened) or the tooth structure.

In another aspect, the present invention provides a method of debonding an orthodontic appliance from a tooth structure. The method includes: providing an orthodontic appliance having a base for bonding the orthodontic appliance to a tooth structure and an orthodontic adhesive on the base; applying the base of the orthodontic appliance to the tooth structure; hardening the orthodontic adhesive; removing the orthodontic appliance from the tooth structure to provide a tooth structure having a hardened orthodontic adhesive remnant thereon; and selectively staining a surface including the orthodontic adhesive remnant or the tooth structure. Preferably the method includes selectively staining to provide a stained surface and an unstained or lightly stained surface. The stained and/or unstained or lightly stained surfaces can be useful for visually identifying the orthodontic adhesive remnant, which can then be removed. In some embodiments, an orthodontic disclosing composition including a colorant can be used for selectively staining a surface including the hardened orthodontic adhesive remnant or the tooth structure.

Advantageously, the present invention provides methods that are easy to use and effective in selectively staining a surface including a tooth and an orthodontic adhesive. Further, the present invention uses orthodontic disclosing compositions that is easily applied and may be re-applied when necessary. The orthodontic disclosing composition may be applied by a wide variety of unit and/or multi-dose applicators including, for example, L-pop type packages (such as described in U.S. Pat. No. 6,105,761 (Peuker et al.)), small spray bottles, small vials, brushes, pre-dosed applicator (such as described in U.S. Pat. No. 6,413,087 (Petrich et al. and 4,952,204 (Korteweg)), trays, and pens. Preferably, the orthodontic disclosing composition is aqueous based, which allows for easy preparation, easy application, easy clean-up, and less irritation to gingival areas. Further, the components may be readily selected by one of skill in the art to provide desirable properties (e.g., viscosity, color level, and light sensitivity).

Other advantages of the methods of the present invention may include, for example, ease of manufacture of the orthodontic disclosing composition, excellent visual differentiation between orthodontic adhesive and the tooth structure in ordinary room light, easy application and clean-up, and minimal irritation.

Definitions

As used herein, "orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e., single or multi-layer adhesives).

As used herein, "tooth structure" refers to surfaces including, for example, natural and artificial tooth surfaces, bone, tooth models, and the like.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked) or solidified.

As used herein, "hardener" refers to something that initiates hardening of a resin. A hardener may include, for example, a polymerization initiator system, a photoinitiator system, and/or a redox initiator system.

As used herein, "photobleachable" refers to loss of color upon exposure to actinic radiation.

As used herein, the term "(meth)acrylate" is a shorthand reference to acrylate, methacrylate, or combinations thereof, and "(meth)acrylic" is a shorthand reference to acrylic, methacrylic, or combinations thereof.

The phrases "a," "an," "the," "at least one," and "one or more" are used herein interchangeably.

As used herein, the recitations of numerical ranges by endpoints include all numbers subsumed within that range (e.g., 1 to 5 includes 1, 1.5, 2, 2.75, 3, 3.80, 4, 5, etc.).

As used herein, the terms "comprises" and variations thereof do not have a limiting meaning where these terms appear in the description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF CERTAIN EMBODIMENTS

The present invention provides a method of identifying an orthodontic adhesive on a tooth structure. The method includes selectively staining a surface including the orthodontic adhesive or the tooth structure. In some embodiments, selectively staining includes applying an orthodontic disclosing composition including a colorant to at least a portion of the orthodontic adhesive and at least a portion of the tooth structure.

The use of an orthodontic disclosing composition can provide color (before actinic radiation exposure) to the orthodontic adhesive and/or the tooth, thereby aiding the practitioner in removing unhardened and/or hardened orthodontic adhesive from the tooth. The method can be particularly useful to the practitioner for not only removing excess adhesive upon application of an orthodontic appliance to a tooth structure, but also for removing remnants of hardened orthodontic adhesive on a tooth structure after debonding an orthodontic appliance.

The orthodontic disclosing composition preferably can provide color contrast between the orthodontic adhesive and the tooth. Preferably the orthodontic disclosing composition does not irritate soft tissues, such as the gums, tongue, and cheek. Useful initial colors may include, for example, pink, red, blue, orange, and green, which tend to provide good color contrast against the tooth.

In one embodiment, the present invention provides a method of identifying an orthodontic adhesive on a tooth structure using an orthodontic disclosing composition that may be light stable. In another embodiment, the present invention provides a method of identifying an orthodontic adhesive on a tooth structure using an orthodontic disclosing composition that may photo-bleach upon exposure to light and/or a pH change. The orthodontic disclosing composition may also contain optional components including, for example, a sensitizer, an initiator, and an electron-donating compound to impart color-changing capability. The orthodontic disclosing composition preferably does not substantially bleach (e.g., visibly bleach) while the orthodontist is working with it under the normal office conditions, i.e., normal lighting, room temperature of 22° C. to 26° C., and normal relative humidity (RH) of 35% RH to 65% RH. In other words, the orthodontic disclosing composition should retain substantially all (at least 30 percent and preferably 80 percent, as measured using a colorimeter) of its initial color while the orthodontist uses it. A typical working time is typically anywhere from 2 to 10 minutes per tooth.

An orthodontic disclosing composition, which is typically a solution, a dispersion, or a suspension, can be applied to at least a portion of the orthodontic adhesive and/or at least a portion of the tooth structure by a variety of application methods known in the art. Useful application methods include, for example, brushing, spraying, immersing, and the use of applicators such as sponges, pens, and the like.

The orthodontic disclosing compositions can be used on a variety of orthodontic adhesives, including unhardened and/or hardened orthodontic adhesives used in either direct or indirect bonding systems. These orthodontic adhesives may include, for example, hydrophilic orthodontic adhesives, hydrophobic orthodontic adhesives, cements, and combinations thereof.

Suitable hydrophilic orthodontic adhesives may include, for example, those available under the trade designations 3M APC PLUS (3M Unitek, Monrovia, Calif.), ASSURE adhesives and sealants (Reliance Orthodontic Products, Inc, Itasca, Ill.), 3M MULTICURE glass ionomer cement (3M Unitek, Monrovia, Calif.), FUJI ORTHO LC (GC America Inc., Aslip, Ill.), and the like.

Suitable hydrophobic orthodontic adhesives may include, for example, those available under the trade designations 3M TRANSBOND XT (3M Unitek, Monrovia, Calif.), APC II (3M Unitek, Monrovia, Calif.), ORMCO ENLIGHT (Sybron Dental Specialties, Orange, Calif.), LIGHT BOND (Reliance Orthodontic Products, Inc, Itasca, Ill.), TRANSBOND LR (3M Unitek, Monrovia, Calif.), CONCISE (3M Unitek, Monrovia, Calif.), and UNITE (3M Unitek, Monrovia, Calif.).

Typically, the orthodontic disclosing compositions include a colorant and may optionally include, for example, a sensitizer, an initiator, and/or an electron-donating compound. The orthodontic disclosing compositions can be solutions, dispersions, and/or suspensions that include water and/or solvent. Examples of suitable solvents may include, for example, ethanol, isopropanol, acetone, and combinations thereof.

The orthodontic disclosing compositions, as disclosed within, may optionally include, for example, water and/or one or more solvents at suitable levels to produce the desired result. In some embodiments, such compositions include at least 1 percent by weight (wt-%), and sometimes at least 5 wt-%, 10 wt-%, 30 wt-%, 50 wt-%, 70 wt-%, or even 90 wt-% water and/or solvent based on the total weight of the orthodontic disclosing composition. In some embodiments, such compositions include at most 99 wt-%, and sometimes at most 98 wt-%, 95 wt-%, or even 92 wt-% water and/or solvent based on the total weight of the orthodontic disclosing composition.

Colorants

The present invention provides a method to selectively stain the orthodontic adhesive and the tooth using an orthodontic disclosing composition that imparts color to the orthodontic adhesive and/or the tooth through the use of a colorant. In some embodiments, the optional sensitizer and/or initiator and/or electron-donating compound may provide some color to the orthodontic disclosing composition. In some embodiments the sensitizer may serve a dual purpose of providing photoactivation and imparting a color to the orthodontic disclosing composition. In other embodiments, a light stable colorant may be used alone or with optional components including, for example, a sensitizer, an initiator, and/or an electron-donating compound.

The orthodontic disclosing compositions typically include one or more colorants at a suitable level to produce the desired result. Such compositions typically include at least 0.0005 wt-%, sometimes at least 0.01 wt-%, and other times at least 0.1 wt-% colorant based on the total weight of the orthodontic disclosing composition. Such compositions typically include at most 10 wt-%, and sometimes at most 5 wt-%, 1 wt-%, or even 0.25 wt-% colorant based on the total weight of the orthodontic disclosing composition. The amount of colorant selected may vary depending on its extinction coefficient, the ability of the human eye to discern the initial color, and the desired color contrast between the orthodontic adhesive and the tooth. The amount of colorant selected should be an amount effective to achieve the desired color.

A colorant can be, for example, a pigment, a dye (including polymeric dyes such as those available under the trade designations PALMER and LIQUITINT from Milliken & Company; Spartanburg, S.C.), or a combination thereof. Food, drug, and cosmetic grade colorants are preferred. The colorants in the orthodontic disclosing composition may be, for example, reactive or photo-bleachable. Non-reactive colorants may be used alone, or in combination with reactive or photo-bleachable colorants to achieve a desired color. In some embodiments, water soluble colorants are preferred for ease in removal with water.

For embodiments in which the orthodontic disclosing solution includes a photo-bleachable dye, the color formation and bleaching characteristics of the photo-bleachable dye can vary depending on a variety of factors such as, e.g., acid strength, dielectric constant, polarity, amount of oxygen, and moisture content in the atmosphere. One can readily determine the bleaching properties of the dye by irradiating the orthodontic disclosing composition and evaluating the change in color.

Suitable colorants that may impart color to the orthodontic disclosing composition may include, for example, methylene blue, amaranth, erythrocin, floxine, rose bengal, acid red, Tartrazine, Sunset Yellow FCF, Fast Green FCF, Brilliant Blue FCF, indigo carmine, phenolphthalain, sulfophthalain, Yale Violet, methyl orange, fluorescein, methyl viologene, indophenol, dimurosbetaine, bromeosin Y, laudamine B, thionine, neutral red, toluidine blue O, indocyanine green, sulfobromophthalain, uranin, lithol rubin B, lake red C, lithol red, tetrachlorotetrabromo fluorescein, brilliant lake red R, deep maroon, toluidine red, tetrabrom fluorescein, fast acid magenta, permanent red, dibromfluorescein, permanent orange, uranine, quinone yellow, alizarin cyanine green F, quinizarine green SS, light green SF yellow, patent blue NA, carbathrene blue, resorcinol brown, alizarin purple SS, brilliant fast scarlet, permanent red F5R, Ponceaux SX, fast red S, oil orange SS, Polar Yellow 5G, fast light yellow 3G, naphthol green B, Guinea Green B, Sudan Blue B, alizarol purple, naphthol blue black, crocin, crocin blue, orange paprica, chlorophyl, cartamine, safflower yellow, beet red, direct fast yellow GC, direct fast orange, direct fast scarlet 4BS, fast red 6BLL, direct sky blue 5B, direct fast turquoise blue GL, direct copper blue 2B, coprantine green G, direct fast black D, milling yellow O, acid brilliant scarlet 3R, acid violet 5B, alizarin direct blue A2G, acid cyanine 6B, acid cyanine 5R, acid cyanine green G, milling brown 3G, acid fast black VLG, acid black WA, cation yellow 3G, cation golden yellow GL, cation flavin 10G, cation yellow 5GL, cation orange R, cation brown 3GL, cation pin FG, cation brilliant red 4G, cation red GTL, cation red BLH, cation red 6B, cation red 5B, cation blue GLH, cation navy blue RHL, alizarine, chrome fast blue MB, chrome fast brown KE, chrome black P2B, chrome black T, fast scarlet G base, naphthol AS, naphthol AS-G, vat yellow GCN, vat orange RRTS, indigo, vat blue RSN, vat blue BC, vat brilliant green FFB, vat olive green B, vat olive T, vat brown R, vat gray M, disperse fast yellow G, disperse pink RF, disperse blue FFR, disperse blue green B, disperse yellow 5G, disperse golden yellow GG, disperse yellow RL, disperse yellow 3G, disperse orange B, disperse yellow brown 2R, disperse fast ruby 3B, disperse fast red FB, disperse red FL, disperse red GFL, disperse brilliant pink REL, disperse violet HFRL, disperse blue FB, disperse turquoise blue GL, disperse navy blue 2GL, disperse developer, erythrosin yellowish blend fluorescent brightener WG, fluorescent brightener ERN, fluorescent brightener AT, fluorescent brightener SA, solvent orange G, solvent fast yellow 3RE, solvent fast red B, solvent fast blue HFL, reactive yellow 3G, reactive orange 2R, reactive red 3B, reactive scarlet 2G, reactive blue 3G, reactive blue R, reactive blue BR, reactive turquoise GF, reactive brilliant blue R, reactive black B, fast yellow G, fast yellow 10 G, disazo yellow AAA, disazo yellow AAMX, flavane yellow, chromophthal yellow GR, methine yellow GR, methine yellow, sunset yellow lake, anthrapyrimidine yellow, isoindolinone yellow R, quinophthalone yellow, dinitroaniline orange, pyrazolone orange, dianidine orange, persian orange lake, benzimidazolone orange HL, perynone orange, pyranthrone orange, parared, naphthol red FRR, toluidine red, naphthol carmine FB, naphthol red M, naphthol red BS, naphthol red RN, pyrazolone red, permanent red 2B, lithol red, lake red C, lake red C, brilliant carmine 6B, brilliant carmine 3B, Bordeaux 10B, von maroon M, brilliant scarlet G, rhodamine 6G lake, mudder lake, thioindigo Bordeaux, naphthol red FGR, brilliant carmin BS, quinacridone magenta, perylene vermillion, naphthol carmin FBB, perylene red BL, chromophthal scarlet, anthrone red, naphthol red F5RK, erythrocin lake, dianthraquinolyl red, perylene red, perylene maroon, benzimidazolone carmin HF4C, perylene scarlet, amaranth lake, quinacridone red E, pyranthron red, rhodamine B lake, methyl violet lake, alizarine maroon lake, quinacridone red, dioxadine violet, thioindigo magenta, Victoria blue lake, Victoria blue 6G lake, phthalocyanine blue, alkali blue G, indanthrone blue, brilliant green lake, malachite green lake, phthalocyanine green, pigment green B, phthalocyanine green 6Y, benzimidazolone brown HFR, aniline black, diarylide yellow H10G, diarylide yellow HR, carbazole violet, metacresol purple, bromophenol blue, crystal violet, gentiana violet, bromocresol green, bromothymol blue, FD & C dyes (e.g., FD&C Blue 1, FD&C Red 3, and FD&C Red 40), alumina lakes, and combinations thereof. Additional colorants include those disclosed in PCT International Publication Nos. WO2004/069944 (Kwan et al.) and WO2004/072194 (Kwan).

Preferred colorants include erythrosin yellowish blend, FD&C Blue 1, Rose Bengal, methylene blue, eosin, and combinations thereof.

When a photo-bleachable dye is used, the color change in the orthodontic disclosing composition may be initiated by light. Preferably the orthodontic disclosing composition's color change is initiated using, for example, a dental light that emits visible or near infrared (IR) light for a sufficient amount of time.

When a pigment is used as the colorant according to the invention, a pigment dispersant may be used in conjunction therewith. Pigment dispersants that may be used include, for example, polymer dispersants, anionic surfactants, cationic surfactants, amphoteric surfactants, nonionic surfactants, and combinations thereof.

Optional Additives

Orthodontic disclosing compositions, as disclosed within, may optionally include for example, sensitizers, initiators, and/or electron-donating compounds.

Sensitizers

The selection of an optional sensitizer may depend to some extent upon the colorant, the initiator, and the electron-donating compound present. Preferably, the sensitizer is capable of light absorption somewhere within the range of wavelengths of 400 to 1200 nanometers, more preferably 400 to 700 nanometers, and most preferably 400 to 600 nanometers.

The sensitizer may act as a colorant in addition to the dye or pigment colorant. For example, camphorquinone may impart a yellow color to the materials of the invention and Rose Bengal may impart a reddish color to the materials. Alternatively, the sensitizer may act to photo-bleach and/or impart a photo-bleached color to the materials of the invention.

Suitable sensitizers may include, for example, compounds in the following categories: ketones, coumarin dyes (e.g., ketocoumarins), xanthene dyes, fluorone acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. Xanthene dyes may include, for example, those dyes whose molecular structure is related to xanthene and have a Color Index number ranging from 45000-45999. Ketones (e.g., monoketones or alpha-diketones), ketocoumarins, aminoarylketones and p-substituted aminostyryl ketone compounds are preferred sensitizers.

For example, a preferred class of ketone sensitizers has the formula:

$$ACO(X)_bB$$

where X is CO or $CR^5R^6$, where $R^5$ and $R^6$ may be the same or different, and may be hydrogen, alkyl, alkaryl or aralkyl, b is zero or one, and A and B may be the same or different and may be substituted (having one or more non-interfering substituents) or unsubstituted aryl, alkyl, alkaryl, or aralkyl groups, or together A and B may form a cyclic structure which may be a substituted or unsubstituted cycloaliphatic, aromatic, heteroaromatic or fused aromatic ring.

Suitable ketones of the above formula may include, for example, monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and combinations thereof.

Suitable diketones may include, for example, aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and combinations thereof.

Suitable alpha-diketones (b=1 and X=CO) may include, for example, 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3, 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and combinations thereof. A preferred sensitizer is 2,3-bornanedione (camphorquinone). In some embodiments, the sensitizer can be a colorant in the disclosing composition.

Orthodontic disclosing compositions may optionally include one or more sensitizers at a suitable level to produce the desired result. In some embodiments, such compositions include at least 0.05 wt-%, more preferably at least 0.1 wt-%, even more preferably at least 0.4 wt-% sensitizer, based on the total weight of the orthodontic disclosing composition. In some embodiments, such compositions include at most 5 wt-%, sometimes at most 1 wt-%, and other times at most 0.75 wt-% sensitizer, based on the total weight of the orthodontic disclosing composition.

Initiators

The selection of an optional initiator may depend to some extent upon the colorant, the sensitizer, and the electron-donating compound chosen.

Suitable initiators may include, for example, mono- and bis-acylphosphine oxides. These initiators may include, for example, those available under the tradename IRGACURE 819, 2005, 2010, and 2010 (Ciba Specialty Chemicals, Tarrytown, N.J.).

Suitable initiators may also include, for example, iodonium salts. Suitable iodonium salts are described in U.S. Pat. No. 3,729,313 (Smith), U.S. Pat. No. 3,741,769 (Smith), U.S. Pat. No. 3,808,006 (Smith), U.S. Pat. No. 4,250,053 (Smith), and U.S. Pat. No. 4,394,403 (Smith). The iodonium salt may be a simple salt (e.g., containing an anion such as $Cl^-$, $Br^-$, $I^-$, $C_4H_9SO_3^-$, $C_4F_9SO_3^-$) or a metal complex salt (e.g., $AsF_6^-$, $SbF_6^-$, and/or partially hydrolyzed forms thereof, e.g., $SbF_5OH^-$). Mixtures of iodonium salts may be used if desired. Preferred iodonium salts may include, for example, diphenyliodonium chloride, diphenyliodonium hexafluorophosphate, diphenyliodonium hexafluoroantimonate, diphenyliodonium tetrafluoroborate, and combinations thereof.

The orthodontic disclosing compositions may optionally include one or more initiators at a suitable level to produce the desired result. In some embodiments, such compositions include at least 0.05 wt-%, sometimes at least 0.25 wt-%, and other times at least 0.7 wt-% initiator, based on the total weight of the orthodontic disclosing composition. In some embodiments, such compositions include at most 5 wt-%, sometimes at most 1 wt-%, even other times at most 0.8 wt-% initiator, based on the total weight of the orthodontic disclosing composition.

Electron-Donating Compounds

The selection of a particular electron-donating compound may depend to some extent upon the colorant, the sensitizer, and the initiator chosen. Suitable electron-donating compounds may include, for example, amines (including, for example, aminoaldehydes and aminosilanes), amides (including, for example, phosphoramides), ethers (including, for example, thioethers), ureas (including, for example, thioureas), ferrocene, sulfinic acids and their salts, salts of ferrocyanide, ascorbic acid and its salts, dithiocarbamic acid and its salts, salts of xanthates, salts of ethylene diamine tetraacetic acid, salts of tetraphenylboronic acid, and triphenyl alkylboronic acid salts. The electron-donating compounds may be unsubstituted or substituted with one or more non-interfering substituents. Preferred electron-donating compounds contain an electron donor atom such as a nitrogen, oxygen, phosphorus, or sulfur atom, and an abstractable hydrogen atom bonded to a carbon or silicon atom alpha to the electron donor atom.

Suitable amine donor compounds may include, for example, alkyl-, aryl-, alkaryl- and aralkyl-amines such as methylamine, ethylamine, propylamine, butylamine, triethanolamine, amylamine, hexylamine, 2,4-dimethylaniline, 2,3-dimethylaniline, o-, m- and p-toluidine, benzylamine, aminopyridine, N,N'-dimethylethylenediamine, N,N'-diethylethylenediamine, N,N'-dibenzylethylenediamine, N,N'-diethyl-1,3-propanediamine, N,N'-diethyl-2-butene-1,4-diamine, N,N'-dimethyl-1,6-hexanediamine, piperazine, 4,4'-trimethylenedipiperidine, 4,4'-ethylenedipiperidine, p-N,N-dimethyl-aminophenethanol and p-N-dimethylamxnobenzonitrile, aminoaldehydes such as p-N,N-dimethylaminobenzaldehyde, p-N,N-diethylaminobenzaldehyde, 9-julolidine carboxaldehyde and 4-morpholinobenzaldehyde, and aminosilanes such as trimethylsilylmorpholine, trimethylsilylpiperidine, bis(dimethylamino)diphenylsilane, tris(dimethylamino)methylsilane, N,N-diethylaminotrimethylsilane, tris(dimethylamino)phenylsilane, tris(methylsilyl)amine, tris(dimethylsilyl)amine, bis(dimethylsilyl)amine, N,N-bis(dimethylsilyl)aniline, N-phenyl-N-dimethylsilylaniline and N,N-dimethyl-N-dimethylsilylamine.

Suitable amide donor compounds may include, for example, N,N-dimethylacetamide, N,N-diethylacetamide, N-methyl-N-phenylacetamide, hexamethylphosphoramide, hexaethylphosphoramide, hexapropylphosphoramide, trimorpholinophosphine oxide and tripiperidinophosphine oxide.

Suitable ether donor compounds may include, for example, 4,4'-dimethoxybiphenyl, 1,2,4-trimethoxybenzene and 1,2,4,5-tetramethoxybenzene.

Suitable urea donor compounds may include, for example, N,N'-dimethylurea, N,N-dimethylurea, N,N'-diphenylurea, tetramethylthiourea, tetraethylthiourea, tetra-n-butylthiourea, N,N-di-n-butylthiourea, N,N'-di-n-butylthiourea, N,N-diphenylthiourea and N,N'-diphenyl-N,N'-diethylthiourea.

Preferred electron-donating compounds include of ethyl-4-dimethylaminobenzoate, ethyl-9,10-dimethoxyanthracene, and combinations thereof.

The orthodontic disclosing compositions may optionally include one or more electron-donating compounds at a suitable level to produce the desired result. In some embodiments, such compositions include at least 0.05 wt-%, sometimes at least 1 wt-%, even other times at least 2 wt-% electron-donating compound, based on the total weight of the orthodontic disclosing composition. In some embodiments, such compositions include at most 10 wt-%, sometimes at most 5 wt-%, and other times at most 3 wt-% electron-donating compound, based on the total weight of the orthodontic disclosing composition.

Optional Miscellaneous Additives

The orthodontic disclosing compositions may also include, for example, additional additives suitable for use in the oral environment. Such additional additives include stabilizers, monomers, oligomers, polymers, and/or fillers as further described herein.

Stabilizers

Suitable stabilizers may include, for example, butylated hydroxyanisole (BHA), butylated hydroxytoluene (BHT), substituted benzophenone, substituted benzotriazoles, hindered amines, and hindered benzoates, available as CYASORB UV (Cytec Industries, West Patterson, N.J.), diethyl-3-acetyl-4-hydroxy-benzyl-phosphonate, 4-dodecyloxy-2-hydroxy benzophenone, paraben, resorcinol monobenzoate, stabilizers available under the trade designations TINUVIN 123, 234, 320, 326, 327, 328, 329, 213 (Ciba Specialty Chemicals Company, Tarrytown, N.Y.), Seesorb 102, 103, 110, 501, 202, 712, 704 (Shipro Kasai, Osaka, JP), IRGANOX 1010, 1076, B215, B220, B225, B900, HP2215, HP2225, HP2251 and HP2921 (Ciba Specialty Chemicals Company, Tarrytown, N.Y.), and combinations thereof.

The orthodontic disclosing compositions may optionally include one or more stabilizers at a suitable level to produce the desired result. In some embodiments, such compositions include at least 0.01 wt-%, sometimes at least 0.1 wt-%, and other times at least 0.5 wt-% stabilizer, based on the total weight of the orthodontic disclosing composition. In some embodiments, such compositions include at most 5 wt-%, sometimes at most 2 wt-%, and other times at most 1 wt-% stabilizer, based on the total weight of the orthodontic disclosing composition.

Monomers, Oligmers, and/or Polymers

Suitable monomers may include, for example, vinyl pyrrolidone, vinyl acetate, polyethylene glycol, methyl methacrylate, methacrylic acid, acrylic acid, and combinations thereof. Suitable oligomers may include, for example, polyethylene oxides, polyvinyl acetates, poly-n-vinylpyrrolidones, polyethylene-glycol monomethacyrlic esters, and combinations thereof. Suitable polymers may include, for example, polyethylene oxides, polyvinyl acetates, poly-n-vinyl pyrrolidones, polyethylene-glycol mono methacrylic esters, and combinations thereof.

The orthodontic disclosing compositions may optionally include one or more monomers, oligomers, and/or polymers at a suitable level to produce the desired result. In some embodiments, such compositions include at least 1 wt-%, sometimes at least 10 wt-%, and other times at least 20 wt-% monomer, oligomer, and/or polymer, based on the total weight of the orthodontic disclosing composition. In some embodiments, such compositions include at most 95 wt-%, sometimes at most 90 wt-%, 80 wt-%, 70 wt-%, 60 wt-%, 50 wt-%, 40 wt-% or even 30 wt-% monomer, oligomer, and/or polymer, based on the total weight of the orthodontic disclosing composition.

Fillers

The orthodontic disclosing compositions, as disclosed within, may optionally include, for example, one or more fillers at a suitable level to produce the desired result. Suitable fillers may include, for example, silane treated and non-silane treated silica, zirconia, fluoroaluminosilicate, fumed silicas, and combinations thereof.

In some embodiments, such compositions include at least 0.01 wt-%, sometimes at least 1 wt-%, and other times at least 10 wt-% filler, based on the total weight of the orthodontic disclosing composition. In some embodiments, such compositions include at most 30 wt-%, sometimes at most 20 wt-%, and other times at most 15 wt-% filler, based on the total weight of the orthodontic disclosing composition.

Additional Optional Miscellaneous Additives

Additional optional miscellaneous additives include, for example, one or more of flavorants, antimicrobials, viscosity modifiers, fluoride releasing materials, pH modifying agents, and surfactants (as disclosed, for example, in U.S. Patent Application Publication No. 2005/0214720 (Milanovich et al.)); anti-bitterness agents (as disclosed, for example, in U.S. Patent Application Publication No. 2005/0203207 (Klettke et al.)); fragrances (as disclosed, for example, in U.S. Pat. No. 6,528,555 (Nikutowski et al.)), and combinations thereof.

The present invention is illustrated by the following examples. It is to be understood that the particular examples, materials, amounts, and procedures are to be interpreted broadly in accordance with the scope and spirit of the invention as set forth herein.

EXAMPLES

The following examples are given to illustrate, but not limit, the scope of this invention. Unless otherwise indicated, all parts and percentages are by weight and all molecular weights are weight average molecular weight. Unless otherwise specified, all chemicals used are commercially available from, for example, Sigma-Aldrich (St. Louis, Mo.).

TABLE 1

Abbreviations, Descriptions and Sources of Experimental Materials

| Abbreviation | Name and Source of Material |
|---|---|
| APC II | An orthodontic adhesive (3M Unitek; Monrovia, CA) |
| APC PLUS | A hydrophilic orthodontic adhesives (3M Unitek; Monrovia, CA) |
| EYB | Erythrosin Yellowish Blend (Sigma-Aldrich; Cat: 23,407-9) |
| CPQ | Camphorquinone (Sigma-Aldrich; Cat: 12,489-3) |
| EDMAB | Ethyl-4-dimethylaminobenzoate (Sigma-Aldrich; Cat: E2, 490-5) |
| DPIHFP | Diphenyliodonium hexafluorophosphate (Johnson Matthey; Cat: 18096) |
| EtOH | Ethanol (Mallinckrodt; Cat: 3791-10) |
| IprOH | Isopropanol (EMD; Cat: 98415) |
| ORTHOLUX LED | ORTHOLUX LED Curing Light (3M Unitek; Monrovia, CA) |
| Peg400DMA | Polyethyleneglycol dimethacrylate (Sartomer; Cat: 603) |
| Blue Food Color | A blue food color concentrate containing FD&C Blue 1 and FD&C Red 40 (McCormick & Co.; UPC 52100-07087) |
| Red Food Color | A red food color concentrate containing FD&C Red 40 and FD&C Red 3 (McCormick & Co., UPC 52100-07091) |
| TRANSBOND XT | A hydrophobic orthodontic adhesive (3M Unitek; Monrovia, CA) |

Preparation of Orthodontic Disclosing Compositions

The components for the orthodontic disclosing compositions A through K as listed in Table 2 were added to separate black jars, and a magnetic stirring bar was added to each jar. The jars were placed in a 40° C. oven for fifteen minutes, and then stirred overnight at room temperature with magnetic stirrers.

Orthodontic disclosing solution L was prepared by combining six drops of Blue Food Color and four drops of Red Food Color in a vial. The dyes were mixed to form a purple concentrate. Approximately one-third (⅓) of the volume of purple concentrate was transferred to another vial and diluted with two times the volume with acetone to give a dark purple orthodontic disclosing solution.

TABLE 2

Orthodontic Disclosing Compositions (components by weight)

| Orthodontic Disclosing Composition | A | B | C | D | E | F | G | H | I | J | K |
|---|---|---|---|---|---|---|---|---|---|---|---|
| EDMAB | 2.172 | 2.170 | 0.935 | 0.935 | 2.172 | 2.170 | — | — | 2.151 | — | — |
| CPQ | 0.483 | 0.483 | 0.208 | 0.208 | 0.483 | 0.483 | — | — | 0.478 | — | — |
| DPIHFP | 0.724 | 0.723 | 0.311 | — | 0.724 | 0.723 | — | — | 0.717 | — | — |
| EYB | 0.024 | 0.095 | 0.041 | 0.041 | 0.024 | 0.092 | — | — | — | — | — |
| Blue Food Color | — | — | — | — | — | — | 0.441 | 0.266 | 0.957 | 1 | 1 |
| Peg400DMA | — | — | — | — | — | — | — | 39.759 | — | — | — |
| Ethanol | 96.598 | 96.529 | 41.575 | 41.575 | — | — | 99.559 | 59.976 | 95.697 | 99 | 49.5 |
| Deionized Water | — | — | 56.930 | 56.930 | — | — | — | — | — | — | 49.5 |
| Isopropanol | — | — | — | — | 96.598 | 96.532 | — | — | — | — | — |

Examples 1-9

The orthodontic disclosing composition was brushed onto unhardened 3M TRANSBOND XT orthodontic adhesive on bovine teeth using a 3M Disposable brush held by a 3M Unitek Brush Holder. The orthodontic disclosing compositions were evaluated for color acceptance of the unhardened orthodontic adhesives vs. the tooth surface. The results are shown in Table 3.

3M Brand APC PLUS Clarity orthodontic brackets were bonded to bovine teeth using 3M TRANSBOND XT orthodontic adhesive. After six hours, the orthodontic brackets were debonded to afford bovine teeth with the hardened orthodontic adhesive pads. The orthodontic disclosing composition was brushed onto the hardened orthodontic adhesive remnant using a 3M Disposable brush held by a 3M Unitek Brush Holder. The orthodontic disclosing compositions were visually ranked from 1 to 4 for color acceptance of the hardened orthodontic adhesive pad and the tooth surface, with 1 having the lowest color acceptance and 4 having the highest color acceptance. The results are shown in Table 3.

Both the teeth and the hardened orthodontic adhesive accepted the orthodontic disclosing compositions in Examples 1-6 and 9 but not in Examples 7 and 8. The application of the orthodontic disclosing composition was limited to the tooth for Example 8.

TABLE 3

Identification of TRANSBOND XT Orthodontic Adhesive on a Tooth Surface

| Example | Orthodontic Disclosing Composition | Color of Orthodontic Disclosing Composition | Color Acceptance of Hardened Adhesive Remnant (3M TBXT Orthodontic Adhesive) | Color Acceptance of Unhardened Orthodontic Adhesive (3M TBXT Orthodontic Adhesive) | Color Acceptance of Tooth | Color Bleaching of Unhardened Adhesive Upon Exposure to ORTHOLUX LED (5 seconds) | Color Removed from Hardened Adhesive and Tooth with Water? |
|---|---|---|---|---|---|---|---|
| 1 | A | Pink | 3 | — | 3 | Yes | Yes |
| 2 | B | Darker Pink | 4 | 4 | 4 | Yes | Yes |
| 3 | C | Darker Pink | 3 | 3 | 3 | Yes | Yes with mild scrub (brush) |
| 4 | D | Pink | 3 | 3 | 3 | No | Yes |
| 5 | E | Pink | 3 | — | 3 | Yes | — |
| 6 | F | Darker Pink | 3 | — | 4 | Yes | — |
| 7 | G | Blue | 1 | — | 1 | No | Yes |
| 8 | H | Blue | 1 | — | 2 | No | Yes |
| 9 | I | Blue | 3 | 3 | 3 w/ or w/o 3M Transbond Plus SEP Primer | No | Yes |

Differences were observed between aqueous and non-aqueous compositions including Blue Food Color and/or Red Food Color. For example, although the aqueous and non-aqueous orthodontic disclosing composition did adsorb to the hardened orthodontic adhesive remnants, the aqueous alcoholic orthodontic disclosing compositions did not wet out and adhere to the tooth surface.

All orthodontic disclosing compositions containing CPQ/EDMAB/DPIHFP adsorbed satisfactorily to both the orthodontic adhesive remnant and the tooth, including the aqueous color changing system. In particular, the addition of this initiator system dramatically improved the adsorption of the food dye to the hardened orthodontic adhesive remnant even though the food dyes were insensitive to light. Without wishing to be bound by theory, it is postulated that the enhancement in adsorption of the food dye to the hardened orthodontic adhesive remnant may be due to the presence of the EDMAB and possibly DPIHFP.

Samples of the teeth with hardened adhesive thereon that had been stained with the orthodontic disclosing solutions were then washed in deionized water for a few minutes and the color of the orthodontic adhesive was evaluated as well as the color of the tooth in white light. Color came off of both the teeth and the hardened orthodontic adhesives. Although the food dyes appear to be slightly easier to remove, the color changing dyes can also be easily removed from both the teeth and the orthodontic adhesives with running water and/or a little scrubbing action.

Fresh samples of the stained hardened remnants described in Examples 1-9 were prepared and tested for light sensitivity. Using an ORTHOLUX LED for 5 seconds, which is the standard bonding time for ceramic brackets, the color bleached beyond detection to the naked eye. Samples typically fade in ambient light (office fluorescent lighting 6-8 foot away from source) within 10-15 minutes. The time to fade may be prolonged by lowering the amount of DPIHFP in the orthodontic disclosing composition.

Examples 10-13

3M Brand APC PLUS Clarity orthodontic brackets were bonded to bovine teeth using 3M APC PLUS orthodontic adhesive. After six hours, the orthodontic brackets were debonded to afford bovine teeth with the hardened orthodontic adhesive pads. The orthodontic disclosing composition was brushed onto the hardened orthodontic adhesive remnant using a 3M Disposable brush held by a 3M Unitek Brush Holder. The orthodontic disclosing compositions were visually ranked from 1 to 4 for color acceptance of the hardened orthodontic adhesive pad and the tooth surface, with 1 having the lowest color acceptance and 4 having the highest color acceptance. The results are shown in Table 4.

Both the teeth and the hardened orthodontic adhesive accepted the orthodontic disclosing compositions in Examples 10, 11 and 13 and not in Example 12. The application of the orthodontic disclosing composition was limited to the orthodontic adhesive remnant for Example 12. The orthodontic disclosing compositions with blue food dyes provided visual color differentiation between the orthodontic adhesive remnants and the teeth in example 11 and was more pronounced in example 12.

Differences were observed between aqueous and non-aqueous compositions including Blue Food Color and/or Red Food Color. For example, although the aqueous and non-aqueous orthodontic disclosing composition did adsorb to the hardened orthodontic adhesive remnants, the aqueous alcoholic orthodontic disclosing compositions did not wet out and adhere to the tooth surface.

All orthodontic disclosing compositions containing CPQ/EDMAB/DPIHFP adsorbed satisfactorily to both the orthodontic adhesive remnant and the tooth, including the aqueous color changing system. In particular, the addition of this initiator system dramatically improved the adsorption of the food dye to the hardened orthodontic adhesive remnant even though the food dyes were insensitive to light. Without wishing to be bound by theory, it is postulated that the enhancement in adsorption of the food dye to the hardened orthodontic adhesive remnant may be due to the presence of the EDMAB and possibly DPIHFP.

Samples of the teeth with hardened adhesive thereon that had been stained with the orthodontic disclosing solutions were then washed in deionized water for a few minutes and the color of the orthodontic adhesive was evaluated as well as the color of the tooth in white light. Color came off of both the teeth and the hardened orthodontic adhesives. Although the food dyes appear to be slightly easier to remove, the color changing dyes can also be easily removed from both the teeth and the orthodontic adhesives with running water and/or a little scrubbing action.

Fresh samples of the stained hardened remnants described in Examples 10-13 were prepared and tested for light sensitivity. Using an ORTHOLUX LED for 5 seconds, which is the standard bonding time for ceramic brackets, the color bleached beyond detection to the naked eye. Samples typically fade in ambient light (office fluorescent lighting 6-8 foot away from source) within 10-15 minutes. The time to fade may be prolonged by lowering the amount of DPIHFP in the orthodontic disclosing composition.

Example 14

Orthodontic disclosing composition L was brushed onto the orthodontic adhesive remnant of a debonded APC PLUS CLARITY bracket (APC PLUS adhesive coated on a CLARITY 6100-601 bracket; 3M Unitek, Monrovia, Calif.). The dark purple orthodontic disclosing composition was quickly

TABLE 4

Identification of APC PLUS Orthodontic Adhesive on a Tooth Surface

Figure 1:
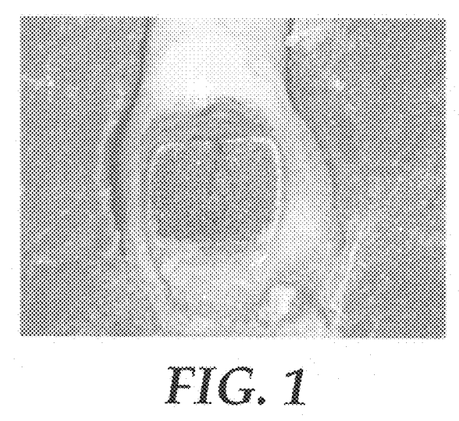
FIG. 1 is a color photograph of an adhesive remnant on a tooth that has been stained as described in Example 14.
Figure 2:
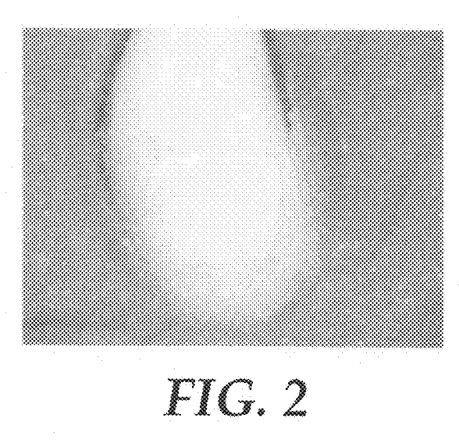
FIG. 2 is a color photograph of an adhesive remnant on a tooth that has not been stained.

| Example | Orthodontic Disclosing Composition | Color of Orthodontic Disclosing Composition | Color Acceptance of the hardened Adhesive Remnant (3M APC PLUS Orthodontic Adhesive) | Color Acceptance of Tooth | Color Bleaching of Unhardened Adhesive Upon Exposure to ORTHOLUX LED (5 seconds) | Color Removed from Hardened Adhesive and Tooth with Water? |
|---|---|---|---|---|---|---|
| 10 | C | Darker Pink | 3 | 3 | Yes | Yes with mild scrub (brush) |
| 11 | J | Blue | 2 | 3 w/ 3M Transbond Plus SEP Primer | No | Yes (Washes from Tooth and Orthodontic adhesive Easily) |
| 12 | K | Blue | 3 | 1 | No | Yes |
| 13 | L | Purple | 3 | 3 | No | Yes | adsorbed by the orthodontic adhesive remnant and the tooth. When the orthodontic adhesive was brushed carefully with the orthodontic disclosing composition, the contrast between colored orthodontic adhesive and tooth was high (as illustrated in the color photograph in FIG. 1) compared to an unstained sample (as illustrated in the color photograph in FIG. 2).

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of identifying a hardened orthodontic adhesive on a tooth structure, the method comprising providing the tooth structure having the hardened orthodontic adhesive disposed thereon, and selectively staining a surface comprising the hardened orthodontic adhesive or the tooth structure, wherein selectively staining comprises applying an orthodontic disclosing composition comprising a colorant to at least a portion of the hardened orthodontic adhesive and at least a portion of the tooth structure in order to identify the hardened orthodontic adhesive.

2. The method of claim 1, wherein the colorant is selected from the group consisting of pigments, food dyes, and combinations thereof.

3. The method of claim 1, wherein the colorant comprises FD&C Blue 1, erythrosin yellowish blend, Rose Bengal, methylene blue, eosin, and combinations thereof.

4. The method of claim 1, wherein the orthodontic disclosing composition further comprises a sensitizer.

5. The method of claim 4, wherein the sensitizer is selected from the group consisting of camphorquinone, methylene blue, and combinations thereof.

6. The method of claim 1, wherein the orthodontic disclosing composition further comprises an initiator.

7. The method of claim 6, wherein the initiator is selected from the group consisting of diphenyliodonium hexafluorophosphate, diphenyliodonium chloride, diphenyliodonium hexafluoroantimonate, and combinations thereof.

8. The method of claim 1, wherein the orthodontic disclosing composition further comprises an electron-donating compound.

9. The method of claim 8, wherein the electron-donating compound is selected from the group consisting of ethyl-4-dimethylaminobenzoate, and ethyl-9,10-dimethoxyanthracene, and combinations thereof.

10. The method of claim 1, wherein the orthodontic disclosing composition is a solution, a dispersion, or a suspension.

11. A method of identifying a hardened orthodontic adhesive on a tooth structure, the method comprising selectively staining the hardened orthodontic adhesive on the tooth structure, wherein selectively staining comprises applying an orthodontic disclosing composition comprising a colorant to at least a portion of the hardened orthodontic adhesive and at least a portion of the tooth structure in order to identify the hardened orthodontic adhesive.

12. A method of identifying remnant hardened orthodontic adhesive on a tooth structure for removal after an orthodontic debonding, the method comprising providing the tooth structure having the remnant hardened orthodontic adhesive disposed thereon, selectively staining the remnant hardened orthodontic adhesive, wherein selectively staining comprises applying an orthodontic disclosing composition comprising a colorant to at least a portion of the remnant hardened orthodontic adhesive and at least a portion of the tooth structure, and removing the remnant hardened orthodontic adhesive.

* * * * *

UNITED STATES PATENT AND TRADEMARK OFFICE
CERTIFICATE OF CORRECTION

| | |
|---|---|
| PATENT NO. | : 8,047,839 B2 |
| APPLICATION NO. | : 11/318174 |
| DATED | : November 1, 2011 |
| INVENTOR(S) | : Brennan et al. |

It is certified that error appears in the above-identified patent and that said Letters Patent is hereby corrected as shown below:

Column 6
Line 20, Delete "phenolphthalain, sulfophthalain," and
insert -- phenolphthalein, sulfonephthalein, --, therefor.
Line 24, Delete "sulfobromophthalain," and insert -- sulfobromophthalein, --, therefor.
Line 27, Delete "dibromfluorescein," and insert -- dibromofluorescein, --, therefor.
Line 35, Delete "chlorophyl, cartamine" and insert -- chlorophyll, carnitine --, therefor.
Line 66, Delete "10 G, and insert -- 10G, --, therefor.
Line 67, Delete "chromophthal" and insert -- cromophtal --, therefor.

Column 7
Line 4, Delete "perynone" and insert -- perinone --, therefor.
Line 13, Delete "chromophthal" and insert -- cromophtal --, therefor.
Line 18, Delete "dioxadine" and insert -- dioxazine --, therefor.

Column 8
Line 44-45, Delete "naphthaquinone, acenaphthaquinone," and
insert -- naphthoquinone, acenaphthoquinone, --, therefor.
Line 46, Delete "bomanedione" and insert -- bornanedione --, therefor.

Column 9
Line 58-59, Delete "dimethylamxnobenzonitrile," and
insert -- dimethylaminobenzonitrile, --, therefor.

Column 11
Line 4, Delete "Oligmers," and insert -- Oligomers, --, therefor.

Signed and Sealed this
Twentieth Day of December, 2011

David J. Kappos
*Director of the United States Patent and Trademark Office*